United States Patent
Mulders et al.

(10) Patent No.: US 8,431,896 B2
(45) Date of Patent: *Apr. 30, 2013

(54) METHOD FOR OBTAINING IMAGES FROM SLICES OF SPECIMEN

(75) Inventors: Johannes Jacobus Lambertus Mulders, Eindhoven (NL); Laurent Roussel, Eindhoven (NL); Wilhelmus Michael Busing, Eindhoven (NL)

(73) Assignee: FEI Company, Hillsboro, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/149,834

(22) Filed: May 31, 2011

(65) Prior Publication Data

US 2011/0226819 A1 Sep. 22, 2011

Related U.S. Application Data

(62) Division of application No. 11/893,022, filed on Aug. 14, 2007, now Pat. No. 7,977,631.

(30) Foreign Application Priority Data

Aug. 16, 2006 (EP) .................................... 06118983

(51) Int. Cl.
*G01N 23/225* (2006.01)
(52) U.S. Cl.
USPC .............................. 250/309; 250/310; 250/307
(58) Field of Classification Search ........... 250/306–311
See application file for complete search history.

(56) References Cited

U.S. PATENT DOCUMENTS 5,024,830 A * 6/1991 Linner ........................ 435/40.52
5,435,850 A 7/1995 Rasmussen
(Continued)

FOREIGN PATENT DOCUMENTS

EP 1801593 12/2005
JP H10-123054 5/1998

OTHER PUBLICATIONS

Denk, Winfried, et al., 'Serial Block-Face Scanning Electron Microscopy to Reconstruct Three-Dimensional Tissue Nanostructure,' PLoS Biol 2, Nov. 2004, pp. 1900-1909, vol. 2, No. 11.

(Continued)

*Primary Examiner* — Jack Berman
*Assistant Examiner* — Eliza Osenbaugh-Stewart
(74) *Attorney, Agent, or Firm* — Scheinberg & Associates; Michael O. Scheinberg; John B. Kelly

(57) ABSTRACT

The invention relates to a method for obtaining images from slices of a specimen, the method comprising: repeatedly obtaining an image of the surface layer of the specimen (1) and removing the surface layer of the specimen, thereby bringing the next slice to the surface; characterized in that after at least one of the removals of a surface layer the specimen is exposed to a staining agent. This method is especially suited for use in a particle-optical instrument equipped with both a scanning electron microscope column (20) and a focused ion beam column (10). The specimen can e.g. be stained in situ by admitting a gas, such as OsO4 (osmiumtetroxide), to the specimen. This method also makes it possible to perform differential staining by first making an image of the specimen exposed to a first staining agent, and subsequently making an image of the specimen when it is additionally stained by a second staining agent.

19 Claims, 2 Drawing Sheets

U.S. PATENT DOCUMENTS

| | | | |
|---|---|---|---|
| 5,698,397 | A | 12/1997 | Zarling et al. |
| 5,851,413 | A | 12/1998 | Casella et al. |
| 6,546,788 | B2 | 4/2003 | Magerle |
| 6,838,380 | B2 | 1/2005 | Bassom et al. |
| 6,888,136 | B2 | 5/2005 | Geurts et al. |
| 7,034,299 | B2 * | 4/2006 | Nakagaki et al. ............. 250/311 |
| 7,103,505 | B2 | 9/2006 | Teshima et al. |
| 7,312,448 | B2 | 12/2007 | Principe |
| 7,317,515 | B2 | 1/2008 | Buijsse et al. |
| 7,348,556 | B2 | 3/2008 | Chitturi et al. |
| 7,463,791 | B2 | 12/2008 | Koehler et al. |
| 7,474,986 | B2 | 1/2009 | Teshima et al. |
| 2005/0199828 | A1 * | 9/2005 | Tokuda et al. ............. 250/492.3 |
| 2009/0220130 | A1 | 9/2009 | Slingerland |
| 2009/0230303 | A1 | 9/2009 | Teshima et al. |

OTHER PUBLICATIONS

Knoche, H., et al, 'Leitfaden der Histologischen Technik in der Licht- und Elektronenmikroskopie fur medizinisch-technische Assistenten,' Gustav Fischer Verlag, 1979, pp. 133-134.

Leighton, Stephen B., 'SEM Images of Block Faces, Cut by a Miniature Microtone Within the SEM-A Technical Note,' Scanning Electron Microscopy, 1981, pp. 73-76, vol. 11.

Weninger, Wolfgang, J., A New Episcopic Method for Rapid 3-D Reconstruction: Applications in Anatomy and Embryology, Anat. Embryol, 1998, pp. 341-348, vol. 197.

Zeiss, Notice of Opposition as filed on EP1890137, Oct. 4, 2011.

Holzer, L., et al., "Three-Dimensional Analysis of Porous BaTiO3 Ceramics Using FIB Nanotomography," Journal of Microscopy, Oct. 2004, pp. 84-95, vol. 216, Pt. 1.

Steer, T.J., et al., "3-D Focused Ion Beam Mapping of Nanoindentation Zones in a Cu-Ti Multilayered Coating," Thin Solid Films, 2002, pp. 147-154, vol. 413.

Brandt, Sami, et al., 'Automatic Alignment of Electron Tomography Images Using Markers,' Proceedings of SPIE, 2000, pp. 277-287, vol. 4197.

Weninger, Wolfgang Johann, et al., 'Phenotyping Transgenic Embryos: a Rapid 3-D Screening Method Based on Episcopic Fluorescence Image Capturing,' Nature Genetics, Dec. 17, 2001, pp. 59-65, vol. 30.

Shimizu, Daisaburo, et al., Three-Dimensional Reconstruction by Scanning Electron Microscopy from Serial Epoxy Resin Semi-Thin Sections After Ion-Etching, Journal of Electron Microscopy, 2001, pp. 51-55, vol. 50., No. 1.

Ewald, Andrew, et al., "Surface Imaging Microscopy, an Automated Method for Visualizing Whole Embryo Samples in Three Dimensions at High Resolution," Developmental Dynamics, 2002, pp. 369-375, vol. 225.

Frank, Joachim, "Electron Tomography, three-dimensional imaging with the transmission electron microscope," 1992, pp. 1-13, 39-60, New York.

Thiberge, Stephan et al., "Scanning electron microscopy of cells and tissues under fully hydrated conditions", Proceedings of the National Academy of Sciences of the United States of America, Mar. 2004, pp. 3346-3351, vol. 101, No. 10.

Gonzalez-Melendi, P., et al., "3-D gold in situ labelling in the EM," The Planet Journal, 2002, pp. 237-243, vol. 29, No. 2.

Heymann, Jurgen A.W., et al., "Site-specific 3D imaging of cells and tissues with a dual beam microscope", Journal of Structural Biology, Jul. 2006, pp. 63-73, vol. 155.

Harrison, C. , et al., "Layer by layer imaging of diblock copolymer films with a scanning electron microscope", Polymer, Elsevier Science Publishers B.V., Jun. 1998, pp. 2733-2744, vol. 39, No. 13.

Scott, John E., et al., "Dermatan Sulphate-Rich Proteoglycan Associates with Rat Tail-Tendon Collagen at the D Band in the Gap Region," Biochemical Journal, 1981, pp. 213-216, vol. 197.

Nagato Y., et al., "Observation on Backscattered Electron Image (BEI) of a Scanning Electron Microscope (SEM) in Semi-Thin Sections Prepared for Light Microscopy," Tokai Journal of Experimental and Clinical Medicine, 1983, pp. 167-174, vol. 8, No. 2.

Translation of Japanese Office Action dated May 22, 2012 for Appl. 2007-211771.

Zeiss, Opposer response to Patent Owner Opposition Response, Jul. 20, 2012, 6 pages.

* cited by examiner

METHOD FOR OBTAINING IMAGES FROM SLICES OF SPECIMEN

This application is a divisional application of U.S. Non-Provisional patent application Ser. No. 11/893,022, filed Aug. 14, 2007, which is hereby incorporated by reference.

TECHNICAL FIELD OF THE INVENTION

The invention pertains to a method for obtaining images from slices of a specimen, the method comprising:
repeatedly
 obtaining an image of the surface layer of the specimen, and
 removing the surface layer of the specimen, thereby bringing the next slice to the surface.

BACKGROUND OF THE INVENTION

Such a method of repeatedly removing a surface layer (also known as slicing) and obtaining an image of a specimen is known from e.g. particle-optical apparatus having both an ion-optical column and an electron-optical column, such as e.g. the DualBeam® instruments commercially available from FEI Company.

It is remarked that 'an image' in the context of this invention is to be interpreted as an image displayed on a display unit as well as a representation thereof in e.g. a computer memory.

Such a method is used in industry and laboratories, e.g. to analyze and inspect biological specimens and polymeric specimens and e.g. to form three-dimensional (3D) reconstructions of structures in biological tissues and polymers.

The instrument used for performing the known method comprises an electron-optical column to obtain an image of a specimen by scanning a focused beam of energetic electrons, typically with an energy between 0.1 to 30 keV, over the specimen. The working of such a column is known from a Scanning Electron Microscope (SEM). Where the beam of electrons impinges on the specimen, secondary radiation, such as secondary electrons, backscattered electron, X-rays and light, may be emitted in response to the bombardment with the impinging electrons. By detecting the amount of e.g. secondary electrons emitted with e.g. a Secondary Electron Detector (SED), (place dependent) information of the surface of the specimen can be obtained. This information can be displayed as an image on a display, or the image can be stored for future retrieval or processing.

After thus obtaining an image of the surface of the specimen, a surface layer may be removed using the ion column. The working of such a column is known from Focused Ion Beam (FIB) instruments. The column emits a focused beam of energetic ions, such as a beam of Ga+ ions with an energy of e.g. 40 keV. Where the beam of ions impinges on the specimen, material is removed. This removal is greatly enhanced by admitting certain gasses in the vicinity where the beam impinges on the specimen. This ion beam can be scanned over the surface, whereby the dwell time (together with the ion beam properties such as current density and energy) determines how much of the surface layer is removed. As a result a slice of material is removed.

After the removal of the surface layer a fresh surface layer is exposed, and with the electron beam an image can be obtained of the thus exposed surface layer. By repeatedly obtaining an image of a surface layer and removing the surface layer from the specimen (removing a slice from the surface layer), a 3D reconstruction of the specimen can be made. Alternatively, a region of interest in the interior of the specimen can be brought to the surface to be examined by techniques that e.g. offer surface information.

A problem when observing certain materials, such as polymers and biological tissues, is that the contrast of the specimen may be too poor to easily differentiate features of the specimen. As known to the person skilled in the art, in order to improve contrast, specimens may be stained to preferentially highlight some parts of the specimen over others. For stains to be effective, they have to preferentially bind to some parts of the specimen, thereby differentiating between different parts of the specimen.

In electron microscopy, heavy metal salts may be used as a staining agent. Such heavy metal salts are commonly derived from gold, uranium, ruthenium, osmium, or tungsten. Heavy ions are used since they will readily interact with the electron beam and produce phase contrast, absorption contrast and/or cause backscattered electrons. Some of these heavy metal salts adhere to specific substances of the specimen. An example of that is $OsO_4$ (osmiumtetroxide), which form a specific chemical reaction with the —C=C— double bonds of unsaturated fatty acids.

Other staining agents that may be used are e.g. compounds of a heavy metal with e.g. an appropriate biologically active group, such as an antibody. Such staining agents are also known as labels. An example is colloidal gold particles absorbed to antibodies. Other examples of this group of staining agents are the Nanogold® particles, produced by Nanoprobes Inc., USA, which may be used to label any molecule with a suitable reactive group such as oligonucleotides, lipids, peptides, proteins, and enzyme inhibitors.

To stain a specimen the specimen is exposed to the staining agent. The exposure can take the form of temporarily immersing the specimen in a liquid, such as a 1% solution of $OsO_4$. Further steps in the staining process may include washing the specimen with water, alcohol, etc. Such staining processes are e.g. described by "Dermatan sulphate-rich proteoglycan associates with rat-tendon collagen at the d band in the gap region", John E. Scott and Constance R. Orford, Biochem. J. (1981) 197, pages 213-216, more specific in the section 'materials and methods'.

The exposure can also take the form of exposing the specimen to a gas or vapour of the staining agent. This is e.g. described in "Observation on backscattered electron image (BEI) of a scanning electron microscope (SEM) in semi-thin sections prepared for light microscopy", Y. Nagata et al., Tokai J. Exp. Clin. Med., 1983 May 8(2), pages 167-174.

For a good contrast the specimen must be sufficiently stained. There is however an optimum in the staining dose: too much staining results in a decrease of the contrast as too much of the specimen becomes stained, whereby the (stained) structures of interest do not stand out to the background anymore. An adequate dose of staining must thus be found.

A problem with certain combinations of staining agents and the materials to be stained is that the diffusion rate of the staining agent in the specimen is very low. Many of the heavy metal staining agents show a low diffusion rate in biological tissues, while in polymers the diffusion rate is even lower. As a result, when e.g. thick polymeric specimens are stained such that the surface is stained to an adequate level, the interior of the specimen is insufficiently stained to obtain a good contrast. If however the staining is such, that the interior is sufficiently stained, the surface is so heavily stained as to be unfit for obtaining a good image. There is therefore a need to stain thick specimens in such a way, that the whole specimen is stained to an adequate level.

The invention intends to provide a method for staining thick specimens in such a way, that the whole specimen can be imaged with an adequate staining level. To that end the method according to the invention is characterized in that, after at least one of the removals of a surface layer the specimen is exposed to a staining agent. By re-staining the surface of the specimen every time that a surface layer is stripped, the surface can be stained to the optimum level as well as a constant level every time.

It is remarked that it might be that re-staining is not necessary after every individual removal of a surface layer, but only after a predetermined number of layers. This may lead to a reduced processing time and thus shorter cycle time.

SUMMARY OF THE INVENTION

In an embodiment of the method according to the invention the images are obtained with a particle-optical apparatus.

Although the method can be used with different kinds of microscopy, such as light microscopy and fluorescent microscopy, it is especially attractive for use with electron and ion microscopy.

It is remarked that, after each removal of a surface layer only a very thin layer of e.g. 20 nm is stained (e.g. by exposing the specimen for a short time to the staining agent), as an additional advantage, the resolution of a Scanning Electron Microscope (SEM) image improves. This can be explained as follows:

Stained specimens in a SEM are often observed by detecting backscattered electrons, as the heavy metals of the staining agent cause much backscattering. Such backscattered electrons can be generated deep within the specimen (e.g. 0.5 μm below the surface) and still be detectable. This implies that, when heavy metal atoms are present deep within the specimen, they are still detected. This results in an image that not only shows information of stained structures at the surface, but also information of stained subsurface structures. By staining only a thin layer of e.g. 20 nm, only stained structures in this thin layer contribute to the image. The light atoms of the unstained specimen cause only very little backscattered electrons and will thus not substantially contribute to the image. The result is thus an image showing only stained structures in the uppermost layer of the specimen, and thus an improved resolution of the image.

The same effect also improves the resolution of e.g. X-rays detected from the specimen, said X-rays being the result of the electron beam impinging on the heavy metal atoms in the stained specimen.

In another embodiment of the method according to the invention the surface layer is removed using a particle beam. Removal of surface layers with an ion beam or an electron beam, assisted with etching gasses, is a well-known technique enabling the removal of layers of e.g. several tens of nanometers, although even thicker layers may be removed. A common thickness of the removed layer is approximately 30 to 60 nm.

In yet another embodiment of the method according to the invention the staining is achieved by exposing the specimen to a gas or vapour. The method is best executed by exposing the specimen to a gas or vapour, so that no further drying of the stripped and re-stained surface is needed. Not only does this offer better results as the specimen does not deform to the repeated wetting and drying, but it also saves time, as staining by wetting followed by rinsing takes typically tens of minutes or more, while exposure to a gas or vapour yields good results in e.g. ten seconds. Another advantage is that it is possible to stain only a very thin layer of the specimen, which results—as mentioned before—in an improved resolution.

In still another embodiment of the method according to the invention, the staining takes place in a vacuum chamber, or at least in a chamber with a low pressure. Staining in a vacuum enables the staining of surfaces that may not be altered by reaction with atmospheric gasses, e.g. a chemical reaction with oxygen or e.g. hydration due to atmospheric water vapour. In other words: the surface of the specimen is kept fresh after the removal of the surface layer.

In a further embodiment of the method according to the invention, the specimen is stained in a vacuum chamber which is part of a particle-optical apparatus.

By exposing the specimen to the staining agent in the vacuum chamber of the particle apparatus, the specimen need not be removed from the apparatus and its position with respect to the columns can be retained. This results in a much reduced processing time, as no time is lost to search for certain features. Also, as the specimen need not be re-positioned in the vacuum chamber (which commonly takes place by venting the vacuum chamber and then mounting the specimen, followed by the evacuation of the chamber) time is saved.

In yet a further embodiment of the method according to the invention, the specimen is exposed to more than one staining agent. A problem known in electron microscopy is that one kind of heavy metal staining agent is not well discernable from another kind of heavy metal marker. Both kinds of heavy metal markers will show the same behaviour: the strong interaction with the electron beam.

It is remarked that it can be envisaged to detect the characteristic X-ray radiation emitted from different heavy metals, but the efficiency of this is much lower than the efficiency of detecting e.g. backscattered electrons, resulting in a lower signal-to-noise ratio when detecting X-rays for a given exposure time to the electron beam. Therefore differential staining (using backscattered electrons) is not well possible in electron microscopy.

By acquiring an image when the specimen is stained with a first staining agent and then acquiring an image of the specimen after it has been stained with a different staining agent, the effect of each staining agent individually can be observed.

The staining agent used for one slice need not be used for another slice. It is conceivable that a first slice is observed using one staining agent, adhering to a certain type of tissue or material, after which a further slice is observed that is stained with another staining agent, adhering with another type of tissue or material. Therefore the method according to the invention also enables differential staining of specimens, using e.g. backscattered electrons.

In still a further embodiment of the method according to the invention, images of the specimen are obtained when the specimen is stained with one staining agent as well as with more than one staining agent, thereby enabling differential staining. By comparing the image obtained when the specimen is stained with one staining agent and the image obtained when the same slice of the specimen is additionally stained with another staining agent, differential staining can be observed.

It is remarked that, by subtracting the image obtained while the specimen is stained by one staining agent from the image obtained while the specimen is additionally stained with another staining agent, thereby eliminating or at least greatly reducing the effect of the first staining agent, the effect of the second staining agent alone can be observed.

In a yet still further embodiment of the method according to the invention, an image of the specimen is obtained when the specimen is stained with one staining agent, after which the surface layer is removed, the specimen is exposed to another staining agent and another image is then obtained, thereby obtaining images of the specimen stained with one staining agent at a time.

In another embodiment of the method according to the invention, an image of the surface layer of the specimen is obtained in unstained condition as well as in stained condition, and the images thus obtained are combined in such a manner that topographical and topological information of the unstained specimen are eliminated, or at least greatly reduced, in the stained image.

In yet another embodiment of the method according to the invention the staining agent comprises a molecule with a heavy metal and an organic group.

In another aspect of the invention a gas injection system is equipped for administering a staining gas or vapour into the vacuum chamber of a particle-optical apparatus.

BRIEF DESCRIPTION OF THE DRAWINGS

The invention will be elucidated on the basis of schematic drawings, where corresponding features are indicated by corresponding reference symbols. To that end, FIG. 1 schematically depicts the method according to the invention, FIG. 2 schematically depicts the method according to the invention, in which differential staining is applied, and FIG. 3 schematically depicts an apparatus equipped to perform the method according to the invention.

DETAILED DESCRIPTION OF THE DRAWINGS

Figure 1:
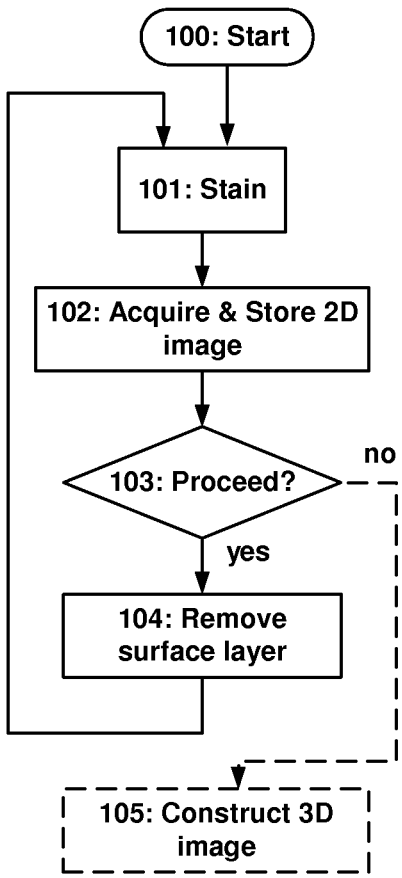

FIG. 1 schematically depicts the method according to the invention. The method starts, after which in step 101 the specimen is stained. An image of the surface of the specimen is acquired and stored in step 102. As long as more slices of the surface must be removed (determined in step 103) a surface layer is removed in step 104.

The decision in step 103 that more slices must be removed can e.g. be based on the structure of interest now being on the surface and visible in the image acquired in step 102, or it can e.g. be based on a predetermined number of slices, equivalent to a certain predetermined thickness of the specimen to be viewed. After the removal of a surface layer in step 104, the specimen is re-stained and a new image is acquired by repeating steps 101, 102 and 103 as long as needed. If no further surface layers need be removed (depending on the decision in step 103), e.g. a 3D image of the specimen may be constructed (step 105).

Figure 2:
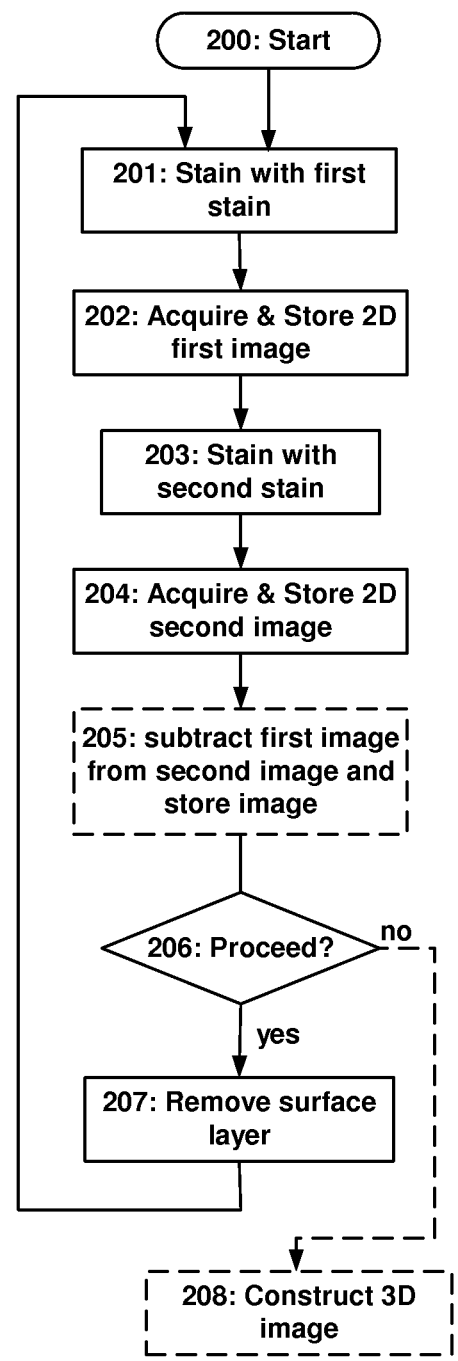

FIG. 2 schematically depicts the method according to the invention, in which differential staining is applied. As in the method described in FIG. 1, the method starts after which in step 201 the specimen is stained with the first staining agent and acquiring a first image of this slice in step 202. Hereafter in step 203 the specimen is stained with another staining agent, the second staining agent. In step 204 a second image of this slice of the thus doubly stained specimen is acquired.

By performing in step 205 suitable image processing, e.g. subtracting the information of the first image of this slice, acquired in step 202, from the second image of this slice acquired in step 204, an image of this slice can be acquired that shows only the information due to the staining with the second staining agent. This greatly simplifies the interpretation of the effect of differential staining.

In step 206, equivalent to step 103 in FIG. 1, a decision is made whether it is necessary to remove a surface layer. If so, the surface layer is stripped in step 207 and the steps 201-206 are repeated, until the result of decision 206 is that no further surface layers need be removed. At the end, in step 207, a 3D image may be constructed of the specimen with any of the stains used, or any combination thereof.

It is remarked that, instead of staining with two different staining agents, this method can also be used to stain with more than two staining agents, resulting in even more information obtained from the specimen. It is also remarked that this method, in which images are subtracted from each other, can also be used to obtain an image of the specimen of one staining agent only, while subtracting topological or other information of the unstained specimen. To achieve this step 201 should be skipped.

Figure 3:
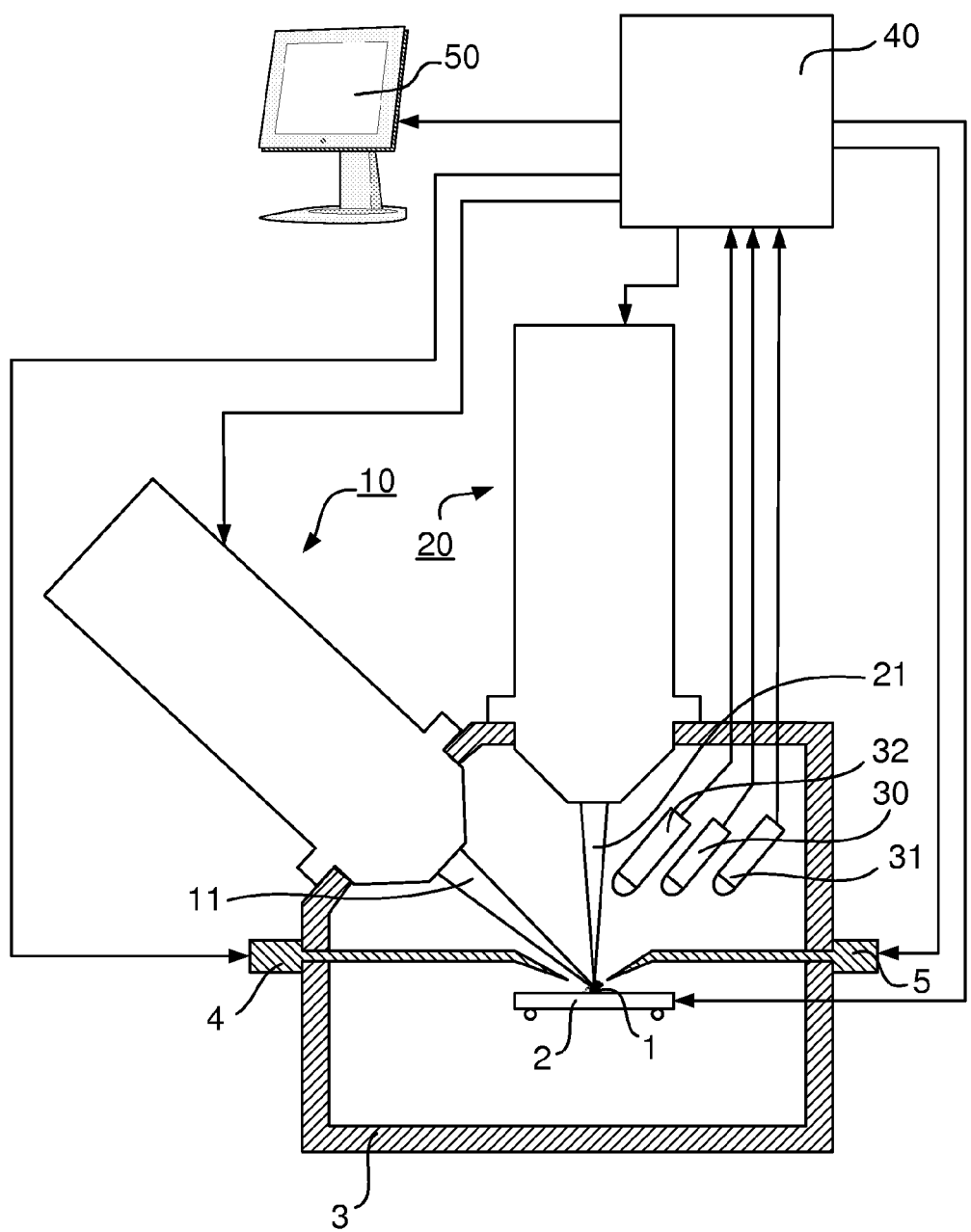

FIG. 3 schematically depicts an apparatus equipped to perform the method according to the invention. FIG. 3 shows a particle-optical apparatus equipped with an ion-optical column 10 producing a focused beam of ions 11, and an electron-optical column 20 producing a focused beam of electrons 21. Both beams 11, 21 can be scanned independently of each other over the specimen 1, said specimen mounted on a specimen stage 2. Also, each of the beams 11, 21 can be blanked at any time so that it is possible to work with one of the beams 11, 21 at a time.

When the specimen 1 is scanned with the electron beam 21 produced by electron optical column 20 in a fashion known from scanning electron microscopy, (place dependent) secondary radiation, is detected, such as secondary electrons detected by a secondary electron detector 30 (SED) of the well-known Everhart-Thornley type. The signal of this detector 30 is used by a Central Control & Processing Unit (CCPU) 40 and an image may be displayed on a viewing screen 50. Also other signals, such as X-rays detected by an X-ray detector 31, or backscattered electrons detected by a Back-Scattered Electron Detector (BSD) 32, may be detected and subsequently processed by CCPU 40. Especially the information detected by the BSD 32 is important, as heavy metal markers cause a large amount of backscattered electrons, and thus a large BSD signal. The CCPU 40 also controls, among others, the ion column 10, electron column 20, the specimen stage 2, a gas injector 4 and staining unit 5.

After obtaining the image of this slice of the specimen, the beam of ions 11 is scanned over the specimen 1, thereby removing the surface layer of the specimen. The removal rate is greatly enhanced by the admission of certain gasses in the vicinity where the ion beam impinges on the specimen. Such gasses can be admitted into the vacuum chamber 3 with the gas injector system 4.

After removing a surface layer and thus exposing a fresh slice of the specimen, the specimen is stained by admitting a staining agent such as OsO4 gas to the specimen. The amount of staining is controlled by the partial vapour pressure as well as the time the specimen is exposed to the vapour. The staining agent is admitted into the vacuum chamber 3 by staining unit 5. The staining is completed by stopping the supply of staining gas or vapour, the remaining staining agent being removed from the vacuum chamber 3 by vacuum pumps (not shown), after which a further image can be obtained in the before mentioned manner.

It is remarked that removal of surface material can also be achieved by an electron beam being scanned over the specimen while certain gasses are admitted. It is further remarked that to remove material the ion beam need not be focused. Also defocused ion beams and e.g. ion bombardment due to gas discharges are known to remove material. However, experimental results show that using a focused ion beam is the preferred method, as scanning the specimen with a focused beam results in a homogeneous removal of material, while otherwise the chance of preferential etching/milling is enhanced, resulting in a non-homogeneous removal of material from the specimen.

It is also remarked that the method according to the invention can e.g. be used to automatically reconstruct a 3D image of the specimen, without human intervention or observation of intermediate images.

We claim as follows:

1. A charged particle system having a charged particle beam source, focusing optics for directing the charged particle beam towards a sample, a detector for forming an image of the sample and arrange to perform the method of:
   repeatedly
   obtaining an image of the surface layer of the specimen;
   removing the surface layer of the specimen, thereby bringing the next slice to the surface; and
   after at least one of the removals of the surface layer the specimen is exposed to a staining agent without the specimen from the system, the staining agent comprises a staining gas or vapor.

2. The system of claim 1 in which the staining gas comprises an OsO4 gas.

3. The system of claim 1 in which the amount of staining of the specimen is controlled by gas or vapor pressure and by the amount of time the specimen is exposed to the gas or vapor.

4. The system of claim 1 in which the staining of the specimen is completed by stopping the supply of staining gas or vapor.

5. A charged particle system having a charged particle beam source, focusing optics for directing the charged particle beam towards a sample, a detector for forming an image of the sample and arranged to perform the method of:
   repeatedly
   obtaining an image of the surface layer of the specimen;
   removing the surface layer of the specimen, thereby bringing the next slice to the surface; and
   after at least one of the removals of the surface layer the specimen is exposed to more than one staining agent without removing the specimen from the system.

6. A system for obtaining images from slices of a specimen, comprising:
   an ion-optical column for providing a beam of ions, said beam of ions used to create a slice of a specimen;
   a detector for detecting secondary radiation emitted from the specimen during a scan; and
   a staining unit to dispense a staining agent, the staining agent exposed to the surface of the specimen.

7. The system of claim 6 further comprising an electron-optical column for providing a focused beam of electrons, said beam of electrons for scanning the specimen and generating secondary radiation from the electron beam impact of the specimen.

8. The system of claim 6 in which the detector comprises an Everhart-Thornley type detector.

9. The system of claim 7 in which the ion beam and the electron beam can be scanned over the specimen independently of each other.

10. The system of claim 9 in which the each of the ion beam and the electron beam can be blanked at any time to allow processing with one of the beams at a time.

11. The system of claim 6 further comprising an X-ray detector or a BackScattered Electron Detector.

12. The system of claim 6 in which the staining agent comprises a staining gas or vapor.

13. The system of claim 12 in which the staining gas comprises an OsO4 gas.

14. The system of claim 12 in which the amount of staining of the specimen is controlled by gas or vapor pressure as well as the time the specimen is exposed to the gas or vapor.

15. The system of claim 12 in which the staining of the specimen is completed by stopping the supply of staining gas or vapor.

16. The system of claim 6 further comprising a vacuum chamber in which specimen is positioned to be processed by the beam of ions, beam of electrons, and one or more staining agents without removing the specimen from the chamber.

17. The system of claim 6 further comprising a gas injector which provides a gas to assist in the removal of material while the electron beam is scanned over the specimen.

18. The system of claim 6 further comprising a Central Control and Processing Unit to receive a signal from the detector and display an image on a viewing screen.

19. The system of claim 6 in which a 3D image of the specimen can be automatically reconstructed.

* * * * *